(12) United States Patent
Joly et al.

(10) Patent No.: US 8,569,537 B2
(45) Date of Patent: Oct. 29, 2013

(54) FUNCTIONALIZED ZIRCONIA NANOPARTICLES AND HIGH INDEX FILMS MADE THEREFROM

(71) Applicant: 3M Innovative Properties Company, St. Paul, MN (US)

(72) Inventors: Guy D. Joly, Shoreview, MN (US); Nathan E. Schultz, Lakeland, MN (US); Encai Hao, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/661,086

(22) Filed: Oct. 26, 2012

(65) Prior Publication Data

US 2013/0046107 A1    Feb. 21, 2013

Related U.S. Application Data (62) Division of application No. 12/947,252, filed on Nov. 16, 2010, now Pat. No. 8,512,464.

(60) Provisional application No. 61/265,968, filed on Dec. 2, 2009.

(51) Int. Cl.
*C07C 275/64* (2006.01)
*C07C 69/52* (2006.01)
*C09D 1/00* (2006.01)
*C07C 229/38* (2006.01)

(52) U.S. Cl.
USPC ....... 560/115; 560/222; 560/125; 106/287.19

(58) Field of Classification Search
None
See application file for complete search history.

(56) References Cited

U.S. PATENT DOCUMENTS

| | | |
|---|---|---|
| 3,893,863 A | 7/1975 | Wilson |
| 5,256,789 A | 10/1993 | Stevens |
| 7,074,463 B2 | 7/2006 | Jones |
| 7,101,618 B2 | 9/2006 | Coggio |
| 7,173,778 B2 | 2/2007 | Jing |
| 7,179,513 B2 | 2/2007 | Jones |
| 7,264,872 B2 | 9/2007 | Walker, Jr. |
| 7,267,850 B2 | 9/2007 | Coggio |
| 7,282,272 B2 | 10/2007 | Jones |
| 7,289,202 B2 | 10/2007 | Groess |
| 7,309,517 B2 | 12/2007 | Jones |
| 7,332,217 B2 | 2/2008 | Coggio |
| 7,491,441 B2 | 2/2009 | Pokorny |
| 7,524,543 B2 | 4/2009 | Jones |
| 7,547,476 B2 | 6/2009 | Jones |
| 7,615,293 B2 | 11/2009 | Farneth |
| 7,622,164 B2 | 11/2009 | Jones |
| 7,649,029 B2 | 1/2010 | Kolb |
| 7,713,597 B2 | 5/2010 | Jones |
| 7,763,331 B2 | 7/2010 | Jones |
| 7,892,638 B2 | 2/2011 | Jones |
| 2005/0249940 A1 | 11/2005 | Klun |
| 2005/0249956 A1 | 11/2005 | Jing |
| 2007/0014018 A1 | 1/2007 | Wheatley |
| 2010/0253885 A1 | 10/2010 | Jones |
| 2011/0103072 A1 | 5/2011 | Jones |

FOREIGN PATENT DOCUMENTS

| | | |
|---|---|---|
| CA | 2210905 A1 | 8/1996 |
| GB | 921536 | 3/1963 |
| JP | 2002-362012 | 12/2002 |
| WO | WO 91/14674 A2 | 10/1991 |
| WO | WO 2009/085926 | 7/2009 |

OTHER PUBLICATIONS

International Search Report for PCT/US2010/057435, pp. 6.
"Surface-Modified Zirconia Nanoparticles", U.S. Appl. No. 61/146,466, filed Jan. 22, 2009.

*Primary Examiner* — Yun Qian
(74) *Attorney, Agent, or Firm* — Steven E. Skolnick (57) ABSTRACT

The present disclosure relates to surface-modified zirconia nanoparticles, methods for making and using the same, and high index of refraction films made therefrom. The provided zirconia nanoparticles are surface modified with ligands that include N-hydroxyurea functionalities. The provided ligands also can contain compatibilizing groups that allow the provided surface-modified zirconia nanoparticles to be incorporated into an organic matrix. High index of refraction films can be made using these organic matrices.

1 Claim, 1 Drawing Sheet

FUNCTIONALIZED ZIRCONIA NANOPARTICLES AND HIGH INDEX FILMS MADE THEREFROM

FIELD

The present disclosure relates to surface-modified zirconia nanoparticles, methods for making and using the same, and high index of refraction films made therefrom.

BACKGROUND

Zirconia nanoparticles have a high refractive index and are useful in organic matrices to alter optical properties of the matrix. For example, zirconia nanoparticles have been used to increase the index of refraction or to increase the x-ray opacity of the organic matrix, while retaining optical transmission. The extent to which the x-ray opacity and/or refractive index of the organic matrix can be increased is dependent on the percent loading of zirconia in the organic matrix and on characteristics of the zirconia particles such as the percent crystallinity, the crystalline structure, the primary particle size, and the degree of association between the primary particles.

Surface modification of zirconia nanoparticles can be used to prevent or reduce particle agglomeration and to enhance the compatibility of the nanoparticles within an organic matrix. Accordingly, zirconia nanoparticles have been treated with a variety of surface modifying agents such as, for example, carboxylic acids, and/or silanes. These traditional surface modifiers have their drawbacks. For example, organic matrices containing acrylic acid-derived residues will displace the zirconia-bound carboxylic acid groups with acrylic acid-derived groups. Silane-functionalized zirconia nanoparticles are thermodynamically unfavorable and experimentally challenging to prepare.

SUMMARY

There is a need for surface-modifiers that can strongly attach to zirconia nanoparticles and do not suffer from the drawbacks of traditional surface modifiers. There is also a need for surface-modified zirconia nanoparticles that are compatible with a variety of organic matrices. There is furthermore a need to have composite materials with enhanced optical properties such as high refractive index or x-ray opacity that include surface-modified zirconia nanoparticles dispersed in organic matrices.

In one aspect, surface-modified nanoparticles are provided that include zirconia nanoparticles and at least one non-metallic organic derivative, comprising at least one N-hydroxyurea functionality, wherein at least some of the non-metallic organic derivatives are attached to at least some of the zirconia nanoparticles.

In another aspect, a method of making surface-modified nanoparticles is provided that includes combining an aqueous sol of acetate-functionalized zirconia nanoparticles with at least one non-metallic organic derivative comprising at least one N-hydroxyurea functionality, or a solution thereof, with a sol to form a mixture and removing water and displaced acetic acid from the mixture to form surface-modified nanoparticles.

In yet another aspect, a composition is provided that includes an organic matrix and surface-modified zirconia nanoparticles attached to at least a portion of the organic matrix, wherein the surface-modified nanoparticles comprise at least one non-metallic organic derivative comprising at least one N-hydroxurea functionality.

Finally, in another aspect, a ligand is provided that includes

In this disclosure:

"high refractive index" refers to materials that have a real component of refractive index above about 1.47;

"N-hydroxyurea functionality" refers to at least one N-hydroxurea group and can refer to the protonated N-hydroxyurea or deprotonated N-hydroxyurea;

"(meth)acrylic" refers to both derivatives of methacrylic acid and/or acrylic acid;

"non-metallic" refers to compounds that do not contain any metal element or metalloid elements such as silicon;

"non-metallic organic derivatives containing N-hydroxyurea functionality" refer to derivatives of N-hydroxyurea that do not contain any metals within or attached to the backbone of the derivative but may include the metal salts of the N-hydroxyurea;

"zirconia" refers to a various stoichiometries for zirconium oxides, most typically $ZrO_2$, and may also be known as zirconium oxide or zirconium dioxide. The zirconia may contain up to 30 weight percent (wt %) of other chemical moieties such as, for example, $Y_2O_3$ and organic material.

The provided surface-modified zirconia nanoparticles, methods, and compositions made therefrom can provide high index transparent films. These films can have an index of refraction of greater than about 1.6 or even higher.

The above summary is not intended to describe each disclosed embodiment of every implementation of the present invention. The brief description of the drawings and the detailed description which follows more particularly exemplify illustrative embodiments.

DETAILED DESCRIPTION

In the following description, reference is made to the accompanying set of drawings that form a part of the description hereof and in which are shown by way of illustration several specific embodiments. It is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Surface-modified nanoparticles are provided that include zirconia nanoparticles. Zirconia nanoparticles can be obtained from zirconia sols that include a plurality of single crystal zirconia particles. In some embodiments, these particles have an average primary particles size of less than 20 nanometers (nm). These sols can be substantially non-associated and can be highly crystalline exhibiting a crystallinity index of about 0.65 or greater. Of the crystalline phase, about 70% or greater can exist in combined cubic and tetragonal crystal lattice structures without a crystal phase stabilizer. Exemplary zirconia sols can be obtained via a hydrothermal method. Zirconia sols and methods of making the same are described, for example, in U.S. Pat. Nos. 6,376,590 (Kolb et al.), 7,241,437, and 7,429,422 (both Davidson et al.). The zirconia nanoparticles in sols of these embodiments can contain yttrium in an amount from about 0.1 wt % to 8 wt % based upon the weight of inorganic oxides in the zirconia particles. The particles can be dispersed in an aqueous medium that includes a carboxylic acid such as, for example, formic acid, acetic acid, propionic acid, butyric acid, or a combination thereof.

The zirconia-containing sols are typically clear. The zirconia-containing sols often have a high optical transmission due to the small size and non-associated form of the primary zirconia particles in the sol. High optical transmission of the sol can be desirable in the preparation of transparent or translucent composite materials. As used herein, "optical transmission" refers to the amount of light that passes through a sample (e.g., a zirconia-containing sol) divided by the total amount of light incident upon the sample. The percent optical transmission may be calculated using the equation $$100(I/I_O)$$

where I is the light intensity passing though the sample and $I_O$ is the light intensity incident on the sample. The optical transmission may be determined using an ultraviolet/visible spectrophotometer set at a wavelength of 600 nm with a 1 cm path length. The optical transmission is a function of the amount of zirconia in a sol. For zirconia-containing sols having about 1 wt % zirconia, the optical transmission is typically at least 70%, at least 80 percent, or at least 90%. For zirconia-containing sols having about 10 wt % zirconia, the optical transmission is typically at least 20%, at least 50%, or at least 70%.

The extent of association between the primary particles can be determined from the hydrodynamic particle size. The hydrodynamic particle size can be measured using Photon Correlation Spectroscopy and is described in more detail in PCT Pat. Publ. No. WO 2009/085926 (Kolb et al.). The term "hydrodynamic particle size" and "volume-average particle size" are used interchangeably herein. If the particles of zirconia are associated, the hydrodynamic particle size provides a measure of the size of the aggregates and/or agglomerates of primary particles in the zirconia sol. If the particles of zirconia are non-associated, the hydrodynamic particle size provides a measure of the size of the primary particles.

A quantitative measure of the degree of association between the primary particles in the zirconia sol is the dispersion index. As used herein the "dispersion index" is defined as the hydrodynamic particle size divided by the primary particle size. The primary particle size (e.g., the weighted average crystallite size) can be determined using x-ray diffraction techniques and the hydrodynamic particle size (e.g., the volume-average particle size) is determined using Photon Correlation Spectroscopy. As the association between primary particles in the sol decreases, the dispersion index approaches a value of 1 but can be somewhat higher. The zirconia-containing nanoparticles typically have a dispersion index of about 1 to 5, about 1 to 4, about 1 to 3, about 1 to 2.5, or about 1 to 2.

Photon Correlation Spectroscopy can be used to further characterize the zirconia particles in the sol. For example, the intensity of the light scattered by particles is proportional to the sixth power of the particle diameter. Consequently, a light-intensity distribution tends to be more sensitive to larger particles than smaller ones. One type of intensity-based size available from Photo Correlation Spectroscopy is the Z-average Size. It is calculated from the fluctuations in the intensity of scattered light using a cumulants analysis. This analysis also provides a value called the polydispersity index, which is a measure of the breadth of the particle size distribution.

The zirconia particles tend to have a Z-average size that is no greater than 70 nanometers, no greater than 60 nm, no greater than 50 nm, no greater than 40 nm, no greater than 35 nm, or no greater than 30 nm. The polydispersity index is often less than 0.5, less than 0.4, less than 0.3, less than 0.2, or less than 0.1. A polydispersity index near 0.5 often indicates a broad particle size distribution while a polydispersity index near 0.1 often indicates a narrow particle size distribution.

In addition to the Z-average size and polydispersity index, a complete light-intensity distribution can be obtained during analysis using Photon Correlation Spectroscopy. This can further be combined with the refractive indices of the particles and the refractive index of the suspending medium to calculate a volume distribution for spherical particles. The volume distribution gives the percentage of the total volume of particles corresponding to particles of a given size range. The volume-average size is the size of a particle that corresponds to the mean of the volume distribution. Since the volume of a particle is proportional to the third power of the diameter, this distribution is less sensitive to larger particles than an intensity-based size. That is, the volume-average size will typically be a smaller value than the Z-average size. The zirconia sols typically have a volume-average size that is no greater than 50 nm, no greater than 40 nm, no greater than 30 nm, no greater than 25 nm, no greater than 20 nm, or no greater than 15 nm. The volume-average size is used in the calculation of the dispersion index.

The zirconia-containing nanoparticles can optionally contain yttrium. Any yttrium that is present is typically in the form of yttrium oxide. The presence of yttrium in the zirconia-containing nanoparticle usually facilitates the formation of the cubic/tetragonal phases rather than the monoclinic phase. The cubic and tetragonal phases are often preferred because they tend to have a higher refractive index and x-ray opacity compared to the monoclinic phase. These phases also tend to be more symmetrical, which can be an advantage in some applications when the zirconia-containing nanoparticles are suspended or dispersed in an organic matrix because they have a minimal effect on the viscosity of the organic matrix. Additionally, the percent loading can be higher with the cubic and tetragonal phases.

The mole ratio of yttrium to zirconium (i.e., moles yttrium÷moles zirconium) in the zirconia-containing nanoparticles is often up to 0.25, up to 0.22, up to 0.20, up to 0.16, up to 0.12, up to 0.08. For example, the mole ratio of yttrium to zirconium can be in the range of from 0 to 0.25, from 0 to 0.22, from 0.01 to 0.22, from 0.02 to 0.22, from 0.04 to 0.22, from 0.04 to 0.20, from 0.04 to 0.16, or from 0.04 to 0.12.

Expressed differently as oxides, the zirconia-containing nanoparticles often contain up to 11 mole percent (mol %) $Y_2O_3$ based on the moles of the inorganic oxides (i.e., $Y_2O_3$ plus $ZrO_2$). For example, the zirconia-containing nanoparticles can contain up to 10 mole percent, up to 8 mole percent, up to 6 mol %, or up to 4 mol % $Y_2O_3$ based on the moles of the inorganic oxides. Some zirconia-containing nanoparticles contain from 0 to 11 mol %, from 0 to 10 mol %, from 1 to 10 mol %, from 1 to 8 mol %, or from 2 to 8 mol % $Y_2O_3$ based on the moles of the inorganic oxides.

Expressed in yet another manner, the zirconia-containing nanoparticles often contain up to 20 weight percent (wt %) $Y_2O_3$ based on the weight of the inorganic oxides (i.e., $Y_2O_3$ plus $ZrO_2$). For example, the zirconia-containing nanoparticles can contain up to 18 wt %, up to 16 wt %, up to 12 wt %, up to 10 wt %, or up to 6 wt % $Y_2O_3$ based on the weight of the inorganic oxides. Some zirconia-containing nanoparticles contain from 0 to 20 wt %, from 0 to 18 wt %, from 2 to 18 wt %, from 2 to 16 wt %, or from 2 to 10 wt % $Y_2O_3$ based on the weight of the inorganic oxides.

The zirconia-containing nanoparticles often contain at least some organic material in addition to inorganic oxides. The organic material can be attached to the surface of the zirconia particles and often originates from the carboxylate species (anion, acid, or both) included in the feedstock or formed as a byproduct of the hydrolysis and condensation reactions. That is, the organic material is often adsorbed to the surface of the zirconia-containing nanoparticles. The zirconia particles often contain up to 15 wt %, up to 12 wt %, up to 10 wt %, up to 8 wt %, or up to 6 wt % organic material based on the weight of the particles.

The zirconia-containing nanoparticles often contain less than 3 milligrams of an alkali metal such as sodium, potassium, or lithium per gram of zirconium in the nanoparticles. For example, the amount of alkali metal can be less than 2 milligrams (mg) per gram of zirconium, less than 1 mg per gram of zirconium, less than 0.6 mg per gram of zirconium, less than 0.5 mg per gram of zirconium, less than 0.3 mg per gram of mg, less than 0.2 mg per gram of zirconium, or less than 0.1 mg per gram of zirconium.

Likewise, the zirconia-containing nanoparticles often contain less than 3 mg of an alkaline earth such as calcium, magnesium, barium, or strontium per gram of zirconium in the nanoparticles. For example, the amount of alkaline earth can be less than 2 mg per gram of zirconium, less than 1 mg per gram of zirconium, less than 0.6 mg per gram of zirconium, less than 0.5 mg per gram of zirconium, less than 0.3 mg per gram of zirconium, less than 0.2 mg per gram of zirconium, or less than 0.1 mg per gram of zirconium.

The zirconia-containing nanoparticles can be substantially crystalline. Crystalline zirconia tends to have a higher refractive index and higher x-ray scattering capability than amorphous zirconia. Due to the difficulty in separately quantifying cubic and tetragonal crystal structures for small particles using x-ray diffraction (i.e., the (111) peak for cubic zirconia often overlaps with the (101) peak for tetragonal zirconia). If yttrium is present, at least 70% of the total peak area of the x-ray diffraction scan is attributed to a cubic structure, tetragonal structure, or a combination thereof with the balance being monoclinic. For example, at least 75%, at least 80%, or at least 85% of the total peak area of some x-ray diffraction scans can be attributed to a cubic crystal structure, tetragonal crystal structure, or a combination thereof. Cubic and tetragonal crystal structures tend to promote the formation of low aspect ratio primary particles having a cube-like shape when viewed under an electron microscope.

The zirconia particles usually have an average primary particle size no greater than 50 nm, no greater than 40 nm, no greater than 30 nm, no greater than 25 nm, no greater than 20 nm, no greater than 15 nm, or no greater than 10 nm. The primary particle size, which refers to the non-associated particle size of the zirconia particles, can be determined by x-ray diffraction.

Nanoparticles, such as zirconia nanoparticles, typically agglomerate and it can be difficult to achieve good dispersions of them in media, such as aqueous or organic media. In particular, it can be difficult to get dispersed nanoparticles within a polymer matrix due to the tendency of the nanoparticles to associate into agglomerates. Therefore, it can be advantageous to modify the surface of the nanoparticles so that agglomeration becomes thermodynamically unfavorable. Surface modification involves reacting the zirconia particles with a surface modification agent or combination of surface modification agents that attach to the surface of the zirconia nanoparticles and that modify the surface characteristics of the zirconia particles.

Surface modification agents can be represented by the formula A-B where the A group is capable of attaching to the surface of a zirconia particle, and where B is a compatibilizing group. The A group can be attached to the surface by absorption, formation of an ionic bond, formation of a covalent bond, or a combination thereof. Suitable examples of A groups include, for example, N-hydroxyureas. The compatibilizing groups B can be reactive or nonreactive and can be polar or nonpolar moieties. Polar compatibilizing groups can include a hydroxyl group, a carboxylic acid group, an amine group, a thiol group, an epoxide group, an aziridine group, an azide group, a halide group, an alkyne group, an olefin group, an acrylate group, a methacrylate group, and combinations thereof.

Nonpolar compatibilizing groups can include an alkyl group, an alkylene group, a heteroalkyl group, an aryl group, an arylene group, and combinations thereof. Of particular importance are surface-modification agents that have compatibilization groups (B) that are compatible with polymeric systems. For example, surface modification agents that have (meth)acrylate compatibilizing groups can be useful to disperse zirconia nanoparticles in (meth)acrylic polymer systems. These agents can be obtained, for example, by reacting hydroxylamine with an isocyanate-functionalized (meth)acrylate compound to obtain (meth)acrylate-functionalized N-hydroxyureas that can bind to zirconia nanoparticles.

N-hydroxyureas are structurally and chemically similar to hydroxamic acids which are a well-studied class of compounds. Hydroxamic acids are known to form self-assembled monolayers on native oxides of metals as described by J. P. Folkers, et al., "Self-Assembled Monolayers of Long-Chain Hydroxamic Acids on Native Oxides of Metals," *Langmuir*, 11, 813 (1998). Both N-hydroxyureas and hydroxamic acids have been used in medicinal chemistry applications. For example, N-hyroxyureas can inhibit many enzymes including proteases, ureases, oxygenases, hydrolases, and peroxidases and can provide antibacterial, antifungal, and insecticidal protection for plants. Synthetically, N-hydroxyureas can be obtained by reaction between a hydroxylamine and a carbonyl-based electrophile, such as an isocyanate or carbamyl chloride. N-hydroxyureas can be made by reacting isocyanates or carbamyl chlorides with hydroxylamines as disclosed, for example, in GB 921,536 (Steinbrunn). Alternatively, coupling reactions between a hydroxylamine and a carbamic acid can be carried out directly using coupling and/or activating agents that are useful in the synthesis of amides. These agents include, for example, carbodiimides.

The provided surface-modified nanoparticles include at least one non-metallic organic derivative that comprises at least one N-hydroxyurea as discussed above. In some embodiments, the surface-modified nanoparticles include at least one non-metallic organic derivative that has the formula:

(I)

In this formula $R_1$ can be hydrogen, an alkyl group, a cycloalkyl group, an aryl group, a heteroaryl group, an alkylaryl group, an alkylheteroaryl group and a heterocycloalkyl group. $R_2$ and $R_3$, independently, can include a moiety selected from hydrogen, alkyl, alkylene, heteroalkyl, aryl, arylene, and combinations thereof. Typically alkyl groups have from about 1 to about 20 carbon atoms and can be branched or unbranched. Cycloalkyl groups typically include 5-12 membered rings such as, for example, cyclopentyl, cyclohexyl, cycloheptyl, cyclooctyl, or cyclododecyl groups. Aryl groups include phenyl, naphthyl, anthracenyl, phenanthenyl, biphenyl, or any other aryl ring systems. $R^2$ can be hydrogen, alkyl, alkylene, heteroalkyl, aryl, arylene, or combinations thereof. Additionally $R^2$ can further include at least one of a hydroxyl, amino, thioether, thiol, carboxy, carbonyl, alkylether, alkynyl, alkenyl, halogen, (meth)acrylate or combination thereof. $R^2$ can also include additional N-hydroxyurea groups.

To make the provided surface-modified zirconia nanoparticles, an aqueous sol of acetate-functionalized zirconia nanoparticles is provided as described above. A solution is mixed with the sol that includes at least one non-metallic organic derivative that includes at least one N-hydroxyurea functionality. The mixture is then, optionally, heated and water and displaced acetic acid is removed from the mixture to form surface-modified zirconia nanoparticles that can be isolated as a powder or slurry. Alternatively, the provided surface-modified zirconia nanoparticles can be made in one pot from 2-isocyanatoethyl methacrylate, hydroxylamine, and acetate-stabilized zirconia nanoparticles as described more fully in the Example section below.

In another aspect, a composition is provided that includes an organic matrix and surface-modified zirconia nanoparticles attached to at least a portion of the organic matrix. The surface-modified zirconia nanoparticles include at least one non-metallic organic derivative that includes at least one N-hyroxyurea functionality. The organic matrix can be any polymer or copolymer matrix. The polymer or copolymer matrix can be derived from monomers, oligomers, copolymers, or a combination thereof. Exemplary polymers include poly(meth)acrylates, polyesters, polyurethanes, polystryenes, epoxies, vinyl polymers, (methacrylated) polyesters, and combinations thereof. The surface-modified zirconia nanoparticle sols can also be combined with other types of polymers, for example, polyolefins, polycarbonates, and polyimides.

In some embodiments, surface-modified zirconia nanoparticles can be dispersed and bonded into optically clear organic matrices to produce high refractive index composites. For example, zirconia nanoparticles that have been surface modified with carboxylates or silanes can be incorporated into organic matrices that contain ultraviolet curable monomers to form materials with refractive indices greater than 1.47. It is contemplated that the provided N-hydroxyurea-functionalized zirconia nanoparticles will be compatible in these systems as well.

Surface-modified zirconia nanoparticles can be produced with small organic ligands attached to the nanoparticles. Typically, all organic films can be produced that have refractive indices as high as about 1.45-1.65 by incorporating aromatic groups, halogens or other groups that have high density and dielectric constant. But it is very hard to make an optically clear polymeric film that has a refractive index much higher than 1.65. Zirconia nanoparticles that have been surface-modified by low molecular weight N-hydroxyureas such as, for example, those made from 2-isocyanatoethyl methacrylate and hydroxylamine, can be incorporated into acrylic films which, after curing, can produce clear films having a refractive index of greater than 1.65, even greater than 1.70. These high index films can be useful to make optical display elements or other optical elements that have low reflection (for example, anti-reflective properties).

Figure 1:
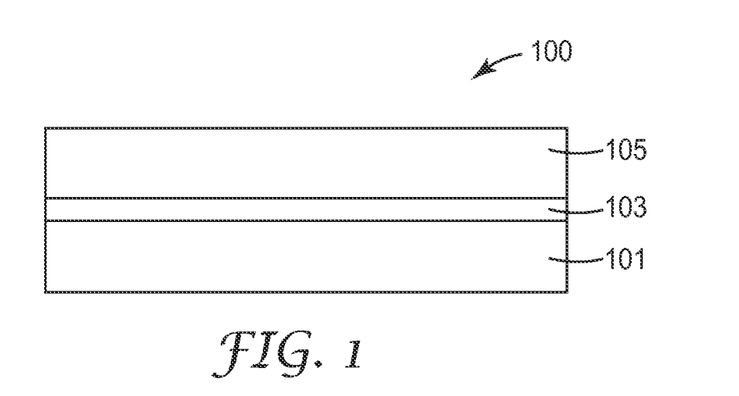
FIG. 1 is a schematic drawing of an embodiment of a provided composition.
Figure 2:
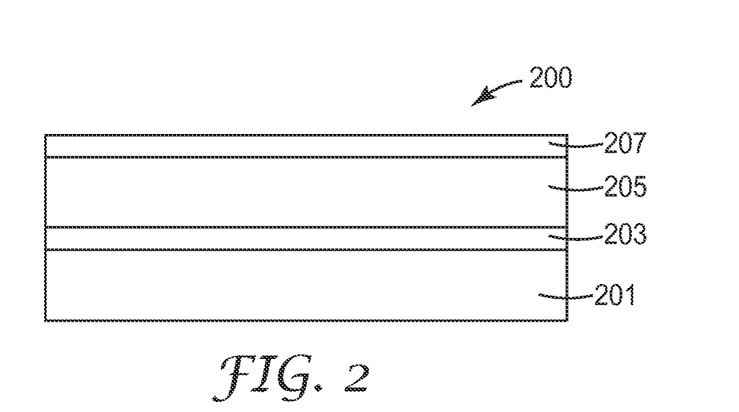
FIG. 2 is a schematic drawing of another embodiment of a provided composition.

FIG. 1 is a schematic of an embodiment of an article that includes provided surface-modified zirconia nanoparticles incorporated into an organic matrix. Article 100 includes optically transmissive substrate 101 that includes primer 103 disposed thereupon. High index of refraction hardcoat 105 is adjacent to and in contact with primer 103. FIG. 2 is a schematic drawing of an embodiment of an article that includes an antireflection film. Article 200 includes substrate 201, primer 203, and high index hardcoat 205 as illustrated in FIG. 1. Atop and in contact with hardcoat 205 is low index optical coating 207. Low index optical coating 207 is a quarter wavelength coating that has an index of refraction of 1.43

In some embodiments, the organic matrix can be an adhesive composition. Typically the adhesive compositions can be (meth)acrylic pressure-sensitive adhesives. The adhesive compositions can be derived from precursors that include from about 75 to about 99 parts by weight of an alkyl acrylate having 1 to 14 carbons in the alkyl group. The alkyl acrylate can include aliphatic, cycloaliphatic, or aromatic alkyl groups. Useful alkyl acrylates (i.e., acrylic acid alkyl ester monomers) include linear or branched monofunctional acrylates or methacrylates of non-tertiary alkyl alcohols, the alkyl groups of which have from 1 up to 14 and, in particular, from 1 up to 12 carbon atoms. Useful monomers include, for example, 2-ethylhexyl(meth)acrylate, ethyl(meth)acrylate, methyl(meth)acrylate, n-propyl(meth)acrylate, isopropyl (meth)acrylate, pentyl(meth)acrylate, n-octyl(meth)acrylate, isooctyl(meth)acrylate, 2-octyl acrylate, isononyl(meth) acrylate, n-butyl(meth)acrylate, isobutyl(meth)acrylate, hexyl(meth)acrylate, n-nonyl(meth)acrylate, isoamyl(meth) acrylate, n-decyl(meth)acrylate, isodecyl(meth)acrylate, dodecyl(meth)acrylate, isobornyl(meth)acrylate, cyclohexyl (meth)acrylate, phenyl meth(acrylate), benzyl meth(acrylate), and 2-methylbutyl(meth)acrylate, biphenyloxyethyl acrylate (BPEA), 6-(2-biphenoxy)hexyl acrylate and combinations thereof.

The provided adhesive composition precursors can also include from about 1 to about 25 parts of a copolymerizable polar monomer such as (meth)acrylic monomer containing carboxylic acid, amide, urethane, or urea functional groups. Useful carboxylic acids include acrylic acid and methacrylic acid. Weak polar monomers like N-vinyl lactams may also be included. A useful N-vinyl lactam is N-vinyl caprolactam. In general, the polar monomer content in the adhesive can include less than about 10 parts by weight or even less than about 5 parts by weight of one or more polar monomers. Useful amides include N-vinyl caprolactam, N-vinyl pyrrolidone, (meth)acrylamide, N-methyl(meth)acrylamide, N,N-dimethyl acrylamide, N,N-dimethyl meth(acrylamide), and N-octyl(meth)acrylamide.

The pressure sensitive adhesive can be inherently tacky. If desired, tackifiers can be added to the precursor mixture before formation of the pressure sensitive adhesive. Useful tackifiers include, for example, rosin ester resins, aromatic hydrocarbon resins, aliphatic hydrocarbon resins, and terpene resins. In general, light-colored tackifiers selected from hydrogenated rosin esters, terpenes, or aromatic hydrocarbon resins can be used.

Other materials can be added for special purposes, including, for example, oils, plasticizers, antioxidants, UV stabilizers, pigments, curing agents, polymer additives, and other additives provided that they do not significantly reduce the optical clarity of the pressure sensitive adhesive.

The provided adhesive compositions (that include surface-modified zirconia nanoparticles) may have additional components added to the precursor mixture. For example, the mixture may include a multifunctional crosslinker. Such crosslinkers include thermal crosslinkers which are activated during the drying step of preparing solvent coated adhesives and crosslinkers that copolymerize during the polymerization step. Such thermal crosslinkers may include multifunctional isocyanates, aziridines, multifunctional (meth)acrylates, and epoxy compounds. Exemplary crosslinkers include difunctional acrylates such as 1,6-hexanediol diacrylate or multi-functional acrylates such as are known to those of skill in the art. Useful isocyanate crosslinkers include, for example, an aromatic diisocyanate available as DESMODUR L-75 from Bayer, Cologne, Germany. Ultraviolet, or "UV", activated crosslinkers can also be used to crosslink the pressure sensitive adhesive. Such UV crosslinkers may include benzophenones and 4-acryloxybenzophenones.

In addition, the precursor mixtures for the provided adhesive compositions can include a thermal or a photoinitiator. Examples of thermal initiators include peroxides such as benzoyl peroxide and its derivatives or azo compounds such as VAZO 67, available from E. I. du Pont de Nemours and Co. Wilmington, Del., which is 2,2'-azobis-(2-methylbutyronitrile), or V-601, available from Wako Specialty Chemicals, Richmond, Va., which is dimethyl-2,2'-azobisisobutyrate. A variety of peroxide or azo compounds are available that can be used to initiate thermal polymerization at a wide variety of temperatures. The precursor mixtures can include a photoinitiator. Particularly useful are initiators such as IRGACURE 651, available from Ciba Chemicals, Tarrytown, N.Y., which is 2,2-dimethoxy-2-phenylacetophenone. Typically, the crosslinker, if present, is added to the precursor mixtures in an amount of from about 0.05 parts by weight to about 5.00 parts by weight based upon the other constituents in the mixture. The initiators are typically added to the precursor mixtures in the amount of from 0.05 parts by weight to about 2 parts by weight. The precursor mixtures can be polymerized and/or cross-linked using actinic radiation or heat to form the adhesive composition as described above and in the Examples below.

The pressure-sensitive adhesive precursors can be blended with the provided surface-modified zirconia nanoparticles to form an optically transparent or translucent mixture. Typically, the mixtures can contain up to about 25 wt % zirconia or even more. The mixture can be polymerized by exposure to heat or actinic radiation (to decompose initiators in the mixture). This can be done prior to the addition of a cross-linker to form a coatable syrup to which, subsequently, one or more crosslinkers, and additional initiators can be added, the syrup can be coated on a liner, and cured (i.e., cross-linked) by an additional exposure to initiating conditions for the added initiators. Alternatively, the crosslinker and initiators can be added to the monomer mixture and the monomer mixture can be both polymerized and cured in one step. The desired coating viscosity can determine which procedure used. The disclosed adhesive compositions or precursors may be coated by any variety of known coating techniques such as roll coating, spray coating, knife coating, die coating, and the like. Alternatively, the adhesive precursor composition may also be delivered as a liquid to fill the gap between the two substrates and subsequently be exposed to heat or UV to polymerize and cure the composition. The thickness of the adhesive layer in the articles of disclosure tends to be greater than about 5 micrometers (μm), greater than about 10 μm, greater than about 15 μm, or even greater than about 20 μm. The thickness is often less than about 1000 μm, less than about 250 μm, less than about 200 μm, or even less than about 175 μm. For example, the thickness can be from about 5 to about 1000 μm, from about 10 to about 500 μm, from about 25 to about 250 μm, or from about 50 to about 175 μm.

In some embodiments, compositions that include surface-modified zirconia nanoparticles can be radioopaque. By radioopaque it is meant that the compositions absorb or scatter X-ray radiation. These materials can be useful, for example, in dental or medical applications.

Objects and advantages of this invention are further illustrated by the following examples, but the particular materials and amounts thereof recited in these examples, as well as other conditions and details, should not be construed to unduly limit this invention.

EXAMPLES

Zirconia nanoparticles were functionalized with methacrylate-functionalized N-hydroxyureas. The functionalized particles were then combined with multifunctional acrylates and a photoinitiator before being cured under UV irradiation. Nanozirconia-filled hardcoats were prepared with refractive indices ranging from 1.699-1.743. The films were clear and colorless.

Preparation of Nanozirconia-Filled High Refractive Index Hardcoats

All polymer anti-reflection films (APAR) were prepared on both cellulose triacetate (TAC) and polyethyleneterephthalate (PET) substrates. The films were clear and colorless. Furthermore, the optical performance of the TAC film was comparable to a control film made using nanozirconia functionalized with 3-(trimethoxysilyl)propyl methacrylate (Table 1). The transmission (95.3%), haze (0.30%) and reflectivity (1.7%) of the experimental film were excellent.

TABLE 1

Optical Characteristics of APAR Films[a]

| | % T | % Haze | % Reflectivity |
|---|---|---|---|
| Experimental APAR[b] | 95.3 | 0.30 | 1.7 |
| Control APAR[c] | 95.2 | 0.23 | 1.7 |

[a] APAR films were prepared on TAC film.
[b] The Experimental APAR was prepared using nanozirconia modified with N-hydroxyurea 1.
[c] The Control APAR was prepared using nanozirconia modified with 3-(trimethoxysilyl)propyl methacrylate.

I. N-Hydroxyurea Synthesis

N-hydroxyureas were synthesized by the straightforward reaction between hydroxylamine and an isocyanate (Scheme (1)). Two representative ligands were synthesized.

(1)

General Procedures.

All reactions were performed in round-bottomed flasks using commercial reagents as received. The flasks were gently sealed with a plastic cap, and the reactions were run under an ambient atmosphere with magnetic stirring.

Materials

Commercial reagents were used as received. SR 399 (dipentaerythritol pentaacrylate) and SR 601 (ethoxylated (4) bisphenol A diacrylate) were obtained from Sartomer. CN4000 is a fluorinated acrylate oligomer with a refractive index of 1.341 and is available from Sartomer. IRGACURE® 2959 (1-[4-(2-Hydroxyethoxy)-phenyl]-2-hydroxy-2-methyl-1-propane-1-one), IRGACURE® 127 (2-Hydroxy-1-{4-[4-(2-hydroxy-2-methyl-propionyl)-benzyl]-phenyl}-2-methyl-propan-1-one), and IRGACURE 184 (1-Hydroxy-cyclohexyl-phenyl-ketone) are available from CIBA Specialty Chemicals. Unstabilized tetrahydrofuran was obtained from EMD Chemicals Inc. 1-Methoxy-2-propanol was purchased from J. T. Baker. Hydroxylamine (as a 50 wt % aqueous solution) was obtained from Alfa Aesar. 2-Isocyanatoethyl methacrylate is available from Sigma-Aldrich. Isophorone diisocyanate was obtained from TCI America.

The $ZrO_2$ aqueous sol used in the below examples was prepared according to the procedure outlined in Example 6 of U.S. Pat. No. 7,429,422 (Davidson et al.). HOSTAPHAN 3SAB is a polyester film available from Mitsubishi Polyester Film, Inc. SILPHAN S36 M74A is a silicone-coated polyester (PET) release liner available from Siliconature. Cellulose triacetate film (TAC film) was obtained from Fujufilm, Tokyo, Japan.

Instrumentation

Proton nuclear magnetic resonance ($^1$H NMR) spectra and carbon nuclear magnetic resonance ($^{13}$C NMR) spectra were recorded on a 400 or 500 MHz spectrometer. Chemical shifts for protons are reported in parts per million downfield from tetramethylsilane and are referenced to residual protium in the NMR solvent ($CHCl_3$: δ 7.26; $(CD_2H)_2SO$: δ 2.50; $CD_2HOH$: δ 3.51). Chemical shifts for carbon are reported in parts per million downfield from tetramethylsilane and are referenced to the carbon resonances of the solvent ($CDCl_3$: δ 77.16; $(CD_3)_2SO$: δ 39.52; $CD_3OD$: δ 49.00). Data are presented as follows: chemical shift, integration, multiplicity (br=broad, s=singlet, d=doublet, t=triplet, q=quartet, quint.=quintuplet, m=multiplet), coupling constants in Hertz (Hz), and assignment. Refractive indices of cured films were measured on a Metricon 2010 Prism Coupler.

1

Preparatory Example of Ligand 1

A 250 mL round-bottomed flask equipped with a magnetic stir bar was charged with a 50 wt % solution of hydroxylamine in water (5.0 mL, 2.80 g, 84.8 mmol). Tetrahydrofuran (85 mL) was added with stirring and the mixture became homogeneous. 2-Isocyanatoethyl methacrylate (12.0 mL, 13.2 g, 84.8 mmol) was added to the reaction mixture over a period of 2 minutes. The reaction vessel was gently capped with a yellow plastic cap. After 18 hours, the clear, colorless, and homogeneous reaction mixture was concentrated approximately to dryness in vacuo to a clear, colorless, viscous liquid. Upon standing, the liquid slowly solidified to provide Ligand 1 (18.9 g, 100 mmol, 118%) as a white solid. The excess mass was due to residual tetrahydrofuran solvent. $^1$H NMR (400 MHz, DMSO) δ 8.60 (1H, s, NHOH), 8.38 (1H, s, NHOH), 6.88 (1H, t, J=5.8 Hz, $NHCH_2$), 6.05 (1H, s, $CH_2$=C), 5.67 (1H, s, $CH_2$=C), 4.09 (2H, t, J=5.7 Hz, $CH_2OC$=O), 3.36-3.28 (2H, m, $CH_2NHC$=O), 1.87 (3H, s, $CH_3$); $^{13}$C NMR (101 MHz, DMSO) δ 166.6, 161.6, 135.9, 125.9, 63.7, 18.1; MS (ES) m/z for $C_7H_{11}N_2O_4$ [M-H]$^-$ calcd. 187.1. found 187.0.

(2)

2
(mixture of isomers)

Preparatory Example of Ligand 2

A 50 mL round-bottomed flask equipped with a magnetic stir bar was charged with isophorone diisocyanate (5.0 mL, 5.25 g, 23.6 mmol). 2-Hydroxyethyl methacrylate (2.86 mL, 3.07 g, 23.6 mmol) was added slowly with stirring over a period of 2 minutes. The reaction was sealed with a rubber septum, placed in an oil bath, and heated to 50° C. with stirring. A 20 gauge needle was added to the rubber septum to vent the reaction to air. After 66 hours, the reaction mixture was cooled to room temperature to provide the product as a clear, colorless, viscous liquid. The reaction product was then used directly in the next reaction.

A 100 mL round-bottomed flask equipped with a magnetic stir bar was charged with tetrahydrofuran (25 mL) and a 50 wt % solution of hydroxylamine in water (1.40 mL, 0.784 g, 23.74 mmol). The crude product from the previous reaction was then slowly added to the stirred reaction via pipette over a period of 5 minutes. Tetrahydrofuran (4×2.5 mL) was used to rinse the flask containing the product from the previous reaction and the rinses were added to the reaction. The reaction was capped with a plastic cap equipped with a 16 gauge needle to vent to air. After 24 hours, the reaction mixture was concentrated in vacuo to a foamy white solid. The product was further dried under high vacuum to provide the desired product 2 as a mixture of isomers (7.99 g, 20.7 mmol, 87.9%) as a white solid. $^1$H NMR (400 MHz, DMSO) analysis of the product was consistent with the desired product as a mixture of isomers.

(3)

Example 1

One-Pot Preparation of Methacrylate-Functionalized Zirconia Nanoparticles with Ligand 1

A 1 L round-bottomed flask equipped with a magnetic stir bar was charged with tetrahydrofuran (250 mL) and a 50 wt % solution of hydroxylamine in water (15.0 mL, 8.40 g, 254 mmol). The reaction was cooled to 0° C. in an ice bath. With stirring, 2-isocyanatoethyl methacrylate (36.0 mL, 39.5 g, 255 mmol) was added slowly to the reaction mixture over a period of 20 minutes. After 2 hours, the ice bath was removed and the reaction was allowed to warm to room temperature. After an additional 1 hour, the reaction was sampled. $^1$H NMR (500 MHz, DMSO) analysis was consistent with clean formation of the desired N-hydroxyurea product, and also showed that the starting material (2-isocyanatoethyl methacrylate) had been consumed. An aqueous solution of acetate-stabilized zirconia (442.62 g sol, 181.66 g $ZrO_2$) was added to the reaction. The reaction mixture was stirred for 20 minutes. Then, 1-methoxy-2-propanol (100 mL) was added. The reaction mixture was concentrated in vacuo to approximately 450 g. Then, the solution was diluted with 1-methoxy-2-propanol to approximately 900 g and concentrated in vacuo to about 430-500 g four times. After the final in vacuo concentration, the mixture was diluted with 1-methoxy-2-propanol to 508 g. The final solution was 42 wt % solids, 33 wt % $ZrO_2$, and 79 wt % of the solids were $ZrO_2$. Based on the percent solids and final mass of solution, the overall yield was 93%. The solution of functionalized zirconia nanoparticles was milky white but well dispersed and stable.

Example 2

Hardcoat Prepared Using Ligand 1

An aqueous solution of acetate-stabilized zirconia (4.00 g sol, 1.65 g $ZrO_2$) was added to a 20 mL glass vial. Ligand 1 (0.434 g, 2.31 mmol) was added and the solution was mixed well. The mixture was sonicated for 45 minutes to provide a solution with a small insoluble flake of ligand remaining 1-methoxy-2-propanol (8.0 mL) was added. The solution was mixed well and sonicated again for 30 minutes to provide a cloudy solution. The mixture was concentrated in vacuo to approximately 4.0 mL as a thick solution. 1-methoxy-2-propanol (8.0 mL) was added, and the solution was mixed well and sonicated again for 25 minutes to provide a cloudy solution. The mixture was concentrated in vacuo to approximately 3-4 mL. SR 399 (0.265 g, 0.505 mmol) and IRGACURE 2959 (0.0360 g, 0.161 mmol) were added. The mixture was sonicated for 10 minutes to provide a slightly cloudy solution. The mass of the solution was 3.9976 g (60 wt % solids, 69 wt % of the solids were $ZrO_2$). A handspread was pulled onto a PET liner (2 mil 3SAB, available from Mitsubishi Polyester Film, Inc.) using a 2 mil gap to provide a clear and colorless wet film. The film was dried at 70° C. for 25 minutes and then cooled to room temperature. A release liner (SILPHAN S36 M74 A 152 mm from Siliconature, Treviso, Italy) was placed on the top of the coating. The film was placed under a lamp ($\lambda$=350 nm) and irradiated for approximately 23 hours. The final cured film was clear, colorless, and transparent. The film was 15±2 µm thick. The refractive index of the film was 1.699.

Example 3

High Index Film

Using the procedure of Example 2, a film was prepared from acetate-stabilized zirconia (4.00 g sol, 1.65 g $ZrO_2$), ligand 1 (0.434 g, 2.31 mmol) SR 399 (0.151 g, 0.288 mmol), and IRGACURE 2959 (0.0360 g, 0.161 mmol). The mass of the final solution was 4.0018 g (57 wt % solids, 73 wt % of the solids were $ZrO_2$). The final cured film was clear, colorless, and transparent. The film was 8.7±1.0 µm thick. The refractive index of the film was 1.721.

Example 4

High Index Film

Using the procedure of Example 2, a film was prepared from acetate-stabilized zirconia (4.00 g sol, 1.65 g $ZrO_2$), ligand 1 (0.434 g, 2.31 mmol) SR 399 (0.0797 g, 0.152 mmol), and IRGACURE 2959 (0.0360 g, 0.161 mmol). The mass of the final solution was 4.0092 g (55 wt % solids, 75 wt % of the solids were $ZrO_2$). The final cured film was clear, colorless, and transparent. The film was 7.1±0.8 µm thick. The refractive index of the film was 1.743.

Example 5

Hardcoat Prepared from Ligand 2

An aqueous solution of acetate-stabilized zirconia (2.00 g sol, 0.821 g ZrO$_2$) was added to a 20 mL glass vial. Ligand 2 (0.395 g, 1.03 mmol) was added and the solution was mixed well. The mixture was sonicated for 15 minutes to provide a homogeneous solution. 1-methoxy-2-propanol (8.0 mL) was added. The solution was mixed well and sonicated again for 15 minutes to provide a well-dispersed solution. The mixture was concentrated in vacuo to approximately 1.5-2.0 mL as a thick solution. SR 399 (0.105 g, 0.200 mmol), IRGACURE 2959 (0.018 g, 0.080 mmol), and 1-methoxy-2-propanol (0.25 mL) were added. The mass of the solution was 2.199 g (61 wt % solids, 39 wt % solvent, 61 wt % of the solids were ZrO$_2$). The mixture was sonicated for 15 min to provide a slightly cloudy solution. A handspread was pulled onto a 2 mil (µm) PET liner (50 3SAB, available from Mitsubishi Polyester Film, Inc., Greer, S.C.) using a 1 mil (25 µm) gap to provide a clear and colorless wet film. The film was dried at 80° C. for 9 minutes and then cooled to room temperature. A release liner (SILPHAN S36 M74 A 152 mm) was placed on the top of the coating. The edges were taped down to seal out air. The film was placed under a lamp (λ=350 nm) and irradiated for approximately 21 hours. The final cured film was clear, colorless, and transparent.

Example 6

Polymeric Anti-Reflection Film

A polymeric anti-reflection film was made using N-hydroxyurea-modified zirconia. A stock solution of nanozirconia functionalized with ligand 1 was prepared. An aqueous sol of acetate-stabilized nanozirconia (50.00 g sol, 20.61 g ZrO$_2$) was added to a 250 mL round-bottomed flask. Ligand 1 (5.431 g, 28.86 mmol) was added and the solution was mixed well. The mixture was sonicated for 75 minutes to provide a well-dispersed homogeneous solution. 1-methoxy-2-propanol (100 mL) was added. The solution was mixed well and sonicated again for 45 minutes to provide a slightly cloudy solution. The mixture was concentrated in vacuo to approximately 50-60 mL as a thick solution. 1-methoxy-2-propanol (100 mL) was added, and the solution was mixed well and sonicated again for 45 minutes to provide a slightly cloudy solution. The mixture was concentrated in vacuo to approximately 50-60 mL. 1-methoxy-2-propanol (100 mL) was added, and the solution was mixed well and sonicated again for 50 minutes to provide a slightly cloudy solution. The mixture was concentrated in vacuo to approximately 50-55 mL. The mass of the solution was 52.5516 g (50 wt % solids, 79 wt % of the solids were ZrO$_2$). The solution of functionalized zirconia nanoparticles was cloudy white but was homogeneously dispersed.

The high index coating formulation was prepared by blending the N-hydroxyurea-functionalized zirconia nanoparticles with acrylate monomers and photoinitiator. Briefly, 15 g of N-hydroxyurea-functionalized nanozirconia (50 wt % solid in 1-methoxy-2-propanol), 0.844 g of SR601 (Sartomer, Exton, Pa.), 0.844 g of SR399 (Sartomer, Exton, Pa.), 0.02 g of IRGACURE 184 (Ciba, High Points, N.C.), and 3.7 g of methyl acetyl ketone, were mixed together with stirring to form a homogenous solution.

The high index coating solution was then applied on top of "MELINEX 618" primed PET films or TAC films using a #9 wire-wound rod (obtained from RD Specialties, Webster, N.Y.), respectively. The resulting films were then dried in an oven at 85° C. for 1 min, then cured using a Fusion UV-Systems Inc. Light-Hammer 6 UV (Gaithersburg, Md.) processor equipped with an H-bulb, operating under nitrogen atmosphere at 75% lamp power at a line speed of 30 feet/min (1 passes). The refractive index of the resulting film was measured as 1.70.

The low index coating formulation was prepared according to U.S. Pat. No. 7,615,293. The low index coating solution (3 wt % solid) was over-coated on the high index coating (prepared as above), using #4 rod and air dried for 2 min. Then resulting films were then cured using a Fusion UV-Systems Inc. Light-Hammer 6 UV (Gaithersburg, Md.) processor equipped with an H-bulb, operating under nitrogen atmosphere at 100% lamp power at a line speed of 10 feet/min (1 passes).

The antireflection films on both TAC and PET were clear and colorless. The optical properties of the film on the TAC liner were measured. The transmission was 95.3%, the haze was 0.3%, and the reflectivity was 1.7%. The film passed color stability testing after 288 hours at 83° C. under 0.5 W/cm$^2$ irradiation.

What is claimed is:
1. A ligand comprising:

* * * * *

UNITED STATES PATENT AND TRADEMARK OFFICE
CERTIFICATE OF CORRECTION

PATENT NO. : 8,569,537 B2  
APPLICATION NO. : 13/661086  
DATED : October 29, 2013  
INVENTOR(S) : Guy D Joly et al.

Page 1 of 2

It is certified that error appears in the above-identified patent and that said Letters Patent is hereby corrected as shown below:

In the Specification

<u>Column 1</u>  
Line 60, Delete "N-hydroxurea" and insert -- N-hydroxyurea --, therefor.

<u>Column 2</u>  
Line 2, Delete "N-hydroxurea" and insert -- N-hydroxyurea --, therefor.

<u>Column 2</u>  
Lines 23-24, Delete "N-hydroxurea" and insert -- N-hydroxyurea --, therefor.

<u>Column 2</u>  
Line 24, Delete "N-hydroxurea" and insert -- N-hydroxyurea --, therefor.

<u>Column 6</u>  
Line 61, Delete "N-hyroxyureas" and insert -- N-hydroxyureas --, therefor.

<u>Column 7</u>  
Line 56, Delete "N-hyroxyurea" and insert -- N-hydroxyurea --, therefor.

<u>Column 7</u>  
Line 61, Delete "polystryenes," and insert -- polystyrenes, --, therefor.

<u>Column 8</u>  
Line 36, Delete "1.43" and insert -- 1.43. --, therefor.

<u>Column 11</u>  
Line 42, Delete "Fujufilm," and insert -- Fujifilm, --, therefor.

Signed and Sealed this  
Twenty-fourth Day of June, 2014

Michelle K. Lee  
*Deputy Director of the United States Patent and Trademark Office*

Column 12
Line 32 (Approx.), Delete "187.1." and insert -- 187.1, --, therefor.

Column 14
Line 17, Delete "remaining" and insert -- remaining. --, therefor.